US005780281A

United States Patent [19]

Yasukawa et al.

[11] Patent Number: 5,780,281
[45] Date of Patent: Jul. 14, 1998

[54] METHOD OF PREPARING A LOW-DENSITY POROUS FUSED-FIBER MATRIX

[75] Inventors: Robert Deane Yasukawa, San Jose; Loretta Jane Cordrey, Livermore, both of Calif.

[73] Assignee: Lockheed Martin Corporation, Bethesda, Md.

[21] Appl. No.: 790,686

[22] Filed: Jan. 29, 1997

Related U.S. Application Data

[62] Division of Ser. No. 234,304, Apr. 28, 1994, Pat. No. 5,629,186.

[51] Int. Cl.$^6$ .............................. C12N 11/14; C12N 5/00; G01N 33/551
[52] U.S. Cl. .................. 435/176; 428/325; 435/174; 435/395; 435/398; 435/815; 436/524; 436/527; 530/811
[58] Field of Search ..................... 435/174, 176, 435/177, 180, 181, 395, 398, 815; 428/325; 525/327.3; 436/524, 527; 530/811

[56] References Cited

U.S. PATENT DOCUMENTS 5,629,186  5/1997  Yasakawa et al. .................. 435/177

Primary Examiner—David M. Naff
Attorney, Agent, or Firm—Peter J. Dehlinger; LeeAnn Gorthey

[57] ABSTRACT

A method is provided for preparing a low density porous rigid fused-fiber matrix having a density of between about 3.5 and 5.5 pounds/cubic foot and a free volume of between about 90–98 volume percent for use as a cell-culture substrate or implant material, or in chromatographic separation of blood cells. The method is carried out by forming a slurry containing (I) silica, alumina or silica and alumina fibers having thicknesses between about 0.5 and 20 μm and lengths between about 1 and 10 mm, and having a fiber:liquid weight ratio of between about 1:25 to 1:70, (ii) a thickening agent to give the slurry a viscosity between about 1,000 and 25,000 centipoise, (iii) boron nitride particles between about 2–12 percent by weight of the total fiber weight, and (iv) a dispersing agent when the slurry contains silica fibers, allowing the slurry to settle in a mold to produce a fiber block, drying the fiber block, and heating the dried fiber block to at least about 2200° F. for a period sufficient to cause the fibers to form the fused-fiber matrix. Graphite or polymer filler elements may be provided in the mold prior to settling of the slurry to form strands or spacers in the fiber block that vaporize during heating to produce channels or plates separated by voids. Two or more slurries can be formed having different fiber thicknesses, densities or compositions to produce a matrix having a discontinuous gradient of density or layers of different compositions.

11 Claims, 10 Drawing Sheets

METHOD OF PREPARING A LOW-DENSITY POROUS FUSED-FIBER MATRIX

This is a division of application Ser. No. 08/234,304, filed Apr. 28, 1994, now U.S. Pat. No. 5,629,186.

FIELD OF THE INVENTION

The present invention relates to a low-density porous matrix, and to a method of making the matrix.

BACKGROUND OF THE INVENTION

Porous biomaterials in use today are extractions from naturally occurring materials such as "coral" or artificially fabricated using polymers and hydroxyapatite formulated structures. These structures are not optimized and heretofore, their porosity and densities may been suboptimal for cell growth. Naturally occurring materials such as "coral" have low porosity and cannot guarantee a permeable open cell matrix free from "cul-de-sac" type cavities.

They have limited bio-compatibility and have resulted in either a pathological response from the body or failure to enhance multi-layer cellular growth. Current biomaterials. are difficult to shape and machine at the use site.

SUMMARY OF THE INVENTION

The invention includes, in one embodiment, a porous matrix composed of fused silica, alumina, or silica and alumina fibers. The matrix is characterized by (a) a rigid, three-dimensionally continuous network of open, intercommunicating voids, (b) a density of between about 3.5 and 5.5 pounds/ft3; and (c) a free volume of between about 90–98 volume percent.

In one embodiment, the fibers have diameters between about 0.5 and 5 µm, and fiber lengths between about 1–10 mm. In an alternative embodiment, the silica fibers have about the same fiber lengths and fiber diameters between about 5 to 20 µm, giving relatively larger pores of voids in the matrix. Alternatively, the matrix may have a gradient of fiber diameters in one of the matrix dimensions, or a gradient of matrix density in one matrix dimension.

Also in a preferred embodiment, the matrix contains between 1–5 percent by weight silicon carbide particles.

For use as a matrix for cell culture, the matrix may have a lattice of internal channels through which liquid medium can be supplied to internal regions of the matrix. In an alternative embodiment for use in cell culture, the matrix may be constructed to include a series of spaced, parallel plates.

For use as a body implantable material, for supporting tissue growth in vivo, the matrix may be coated with a biocompatible material at its outer surface. For use as a bioimplantable material for bone growth, the silica fibers may be derivatized with a bone osteogenic factor.

For use in affinity chromatography, the silica fibers may be derivatized with molecules effective to bind ligand molecules passed through the matrix.

For use in a blood diagnostics assay in which a blood sample applied to one region of the matrix is chromatographically separated into blood cells and cell-free serum, the matrix may further include a detection region at which a selected analyte in serum can be detected.

In another aspect, the invention includes a method of producing a rigid fused silica, alumina, or silica and alumina fiber matrix of the type described above. The method includes forming a slurry composed of (i) silica, alumina, or silica and alumina fibers having selected fiber thicknesses in the size range between about 0.5 and 20 µm and fiber lengths between about 1 and 10 mm, at a fiber: liquid weight ratio of between about 1:25 to 1:70, (ii) a viscosity agent effective to give the slurry a viscosity between about 1,000 and 25,000 centipoise, (iii) boron nitride particles, in an amount between about 2–12 percent by weight of the total fiber weight, and (iv) where the fibers include silica fibers, a dispersing agent effective to enhance the dispersion of the silica fibers in the slurry.

The slurry is allowed to settle under conditions effective to produce a fiber block having a selected fiber density between about 3.3 and 5.3 pounds/ft$^3$, and the block is then dried to form a rigid, substantially dehydrated fiber block. This block is heated to a temperature of at least about 2200° F. for a period sufficient to cause the silica fibers to form a fused-fiber matrix.

The slurry may be formed with fibers having a selected fiber thickness, in a selected size range between about 1–20 µm, to achieve a selected pore size in the matrix. The slurry may also include silicon carbide in an amount between 1–5 percent of the total fiber weight.

The boron nitride is preferably present as 15 to 60 µm size particles, and the viscosity agent is preferably one, such as methyl cellulose, effective to enhance binding of boron nitride to the fibers.

The slurry may be allowed to settle under conditions that produce a fiber density gradient in the direction of settling. Alternatively, in forming a density or compositional matrix gradient, two or more different slurries may be poured and allowed to settle successively. For use as a matrix for cell culture, the dehydrated block may be formed to include a lattice of linked strands of graphite or polymer which, during the heating step, vaporize to leave a lattice of interconnected channels through which liquid medium can be circulated through the interior of the matrix.

In still another aspect, the invention includes a method of fractionating blood into cell and serum components. The method includes placing a blood sample at one end of an elongate strip of porous matrix of the type described above, and allowing the sample to migrate by capillarity toward the other end of the strip, wherein migration of cell particle components in the blood is retarded by the network fibers, producing a chromatographic separation of faster-migrating serum and slower-migrating cells.

Also contemplated by the invention is a fibrous matrix comprising a porous matrix composed of fused polymer fibers. The matrix is characterized, in dry form, by: (a) a rigid, three-dimensionally continuous network of open, intercommunicating voids, and (b) a free volume of between about 90–98 volume percent, and silica and/or alumina fibers or particles attached to the polymer fibers.

These and other objects and features of the invention will become more fully apparent when the following detailed description of the invention is read in conjunction with the accompanying drawings.

DETAILED DESCRIPTION OF THE INVENTION

I. Fiber Matrix

Figure 1A:
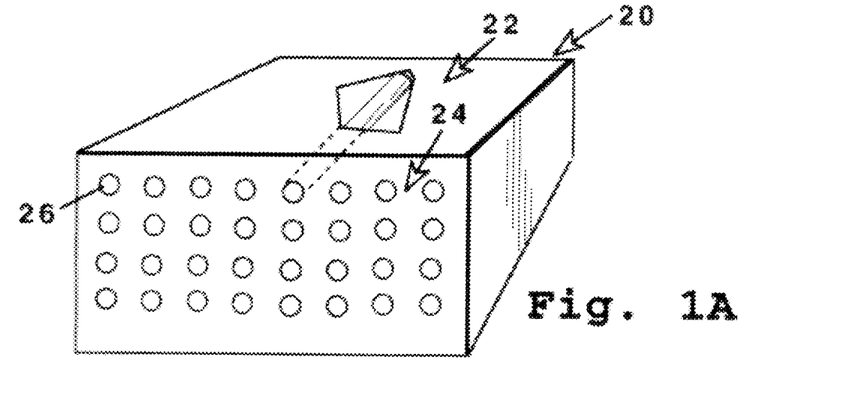
FIGS. 1A and 1B illustrate two embodiments of a fused-silica matrix constructed in accordance with the invention, with portions cutaway to show internal features of the first matrix.
Figure 1B:
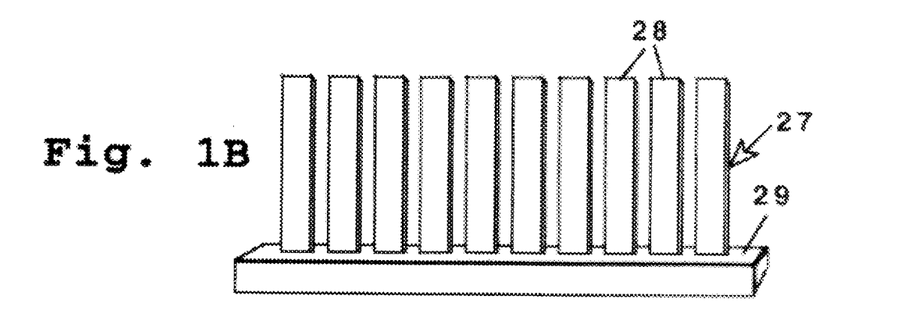

Figs. 1A and 1B illustrate two embodiments of a fused-fiber matrix constructed in accordance with the invention. Each matrix is composed of fused silica, alumina, or silica and alumina fibers, such as will be described below with reference to FIGS. 2A–2D, and is characterized by (a) a rigid, three-dimensionally continuous network of open, intercommunicating voids, (b) a density of between about 3.5and 5.5 pounds/ft3; and (c) a free volume of between about 90–98 volume percent. Other ceramic fibers, such as zirconia or titania, may be used in combination with silica and/or alumina fibers in the matrix.

The nature of the fused-fiber matrix network will be seen below with respect to FIGS. 2A–2D. The matrix density of between 3.5 and 5.5 pounds/ft$^3$ refers to the density of the matrix in fused form. The free volume of the matrix refers to the void volume of the matrix as measured, for example, by the volume of water that can be taken up by a ft$^3$ of the matrix. To illustrate, a free volume of 90 percent means that the total volume occupied by the matrix fibers is 10% and the total volume that could be occupied by a liquid is 90%.

The matrix in FIG. 1A, indicated at 20, is formed of a fused-fiber block 22 containing an array 24 of tubular channels, such as channels 26, extending through the block. The array alloys fluid circulation in interior regions of the block, as will be described below.

The matrix in FIG. 1B, indicated at 27, is formed of a series of thin plates, such as plates 28, having the fused-fiber matrix construction of the invention. The plates have a preferred thickness between about 1 to 5 mm or greater, with a comparable spacing between the plates. A base 29 in the matrix used to support the plates as indicated.

Figure 2A:
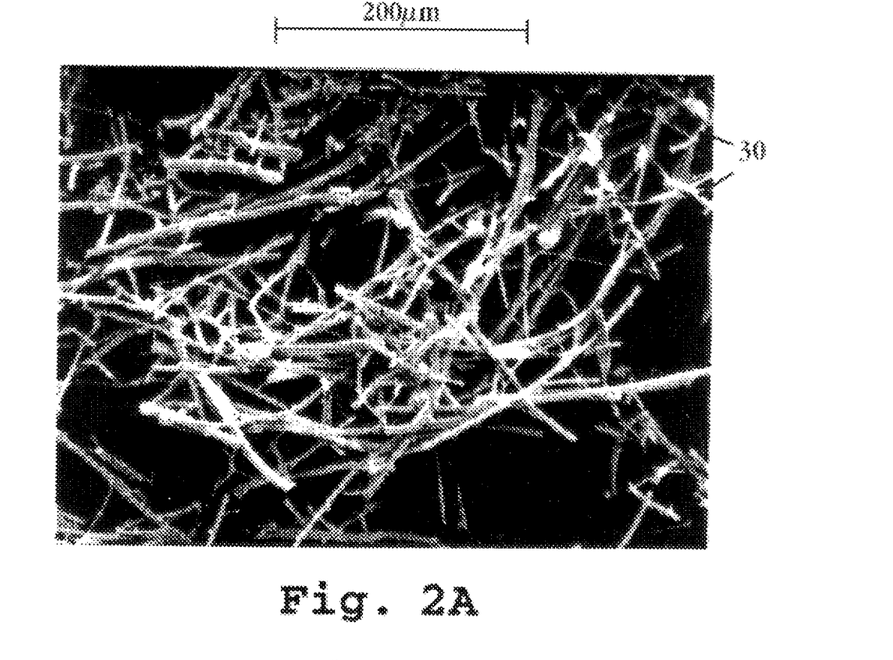
FIGS. 2A–2D show computer generated images of scanning electron micrographs of the FIG. 1 matrix taken at magnifications of 220 (2A), 1,000 (2B), 3,000 (2C), and 7,000 (2D)
Figure 2B:
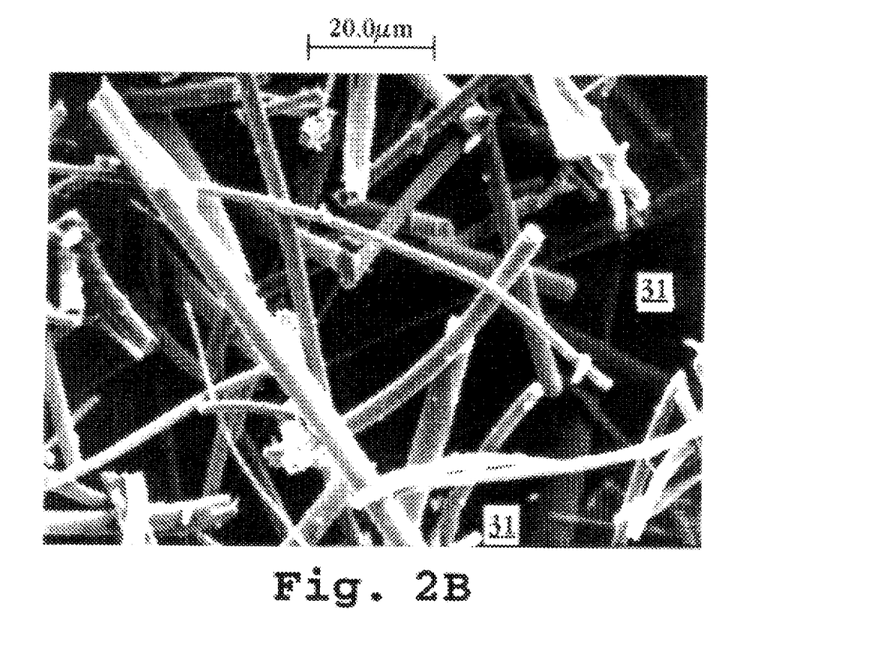

FIGS. 2A–2D are computer generated images of scanning electron microscopy (SEM) photomicrographs of a fused-fiber matrix composed of about 80 percent of fiber weight of silica fibers and 20 percent by fiber weight of alumina fibers, taken at 200×(2A), 1,000×(2B), 2,000×(2C), and 7,000× (2D) magnification. The portion of the matrix shown in FIG. 2A, shows a "nest" of fused silica and alumina fibers, such as fibers 30, ranging in size from about 200 µm to 10 mm in length. The higher magnification SEM micrograph seen in FIG. 2B shows how the fibers are fused at their points of intersection to form a rigid fiber structure having 3-dimensionally continuous network of interconnecting voids or pores, such as voids 31, which tend to have "long"(uninterrupted) dimensions between about 10–100 µm. That is, the fused fibers are substantially randomly oriented, forming in all directions, interconnecting voids defined by groups of fused fibers.

The 2,000×magnification micrograph (FIG. 2C) clearly shows both silica fibers, such as fibers 32, which are smooth surfaced, and alumina fibers, such as fibers 34. The silica fibers have diameters predominantly in the 1.0–1.3 µm size range, and the alumina fibers, in the 2.5–3.5 µm size range. The mottled regions on the alumina fibers, such as region 36 in fiber 34, presumably represent grain growth that occurs during the high-temperature sintering step used in forming the matrix. Clearly visible in FIG. 2C are fusion junctions between two silica fibers, such as junction 38 between silica fibers 32, 40; fusion junctions between silica and alumina fibers, such as junction 44 between silica fiber 32 and alumina fiber 34; and fusion junctions between two alumina fibers, such as junction 46 between alumina fibers 34, 48.

Figure 2C:
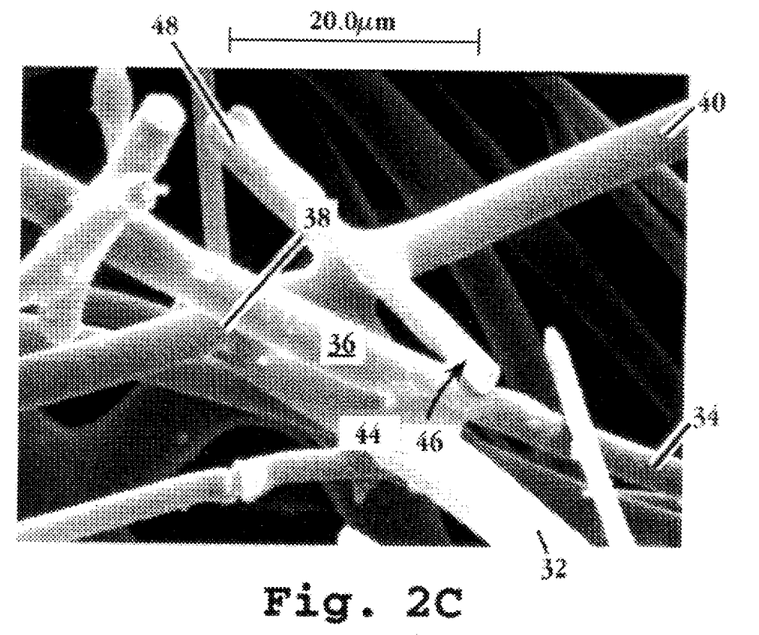
Figure 2D:
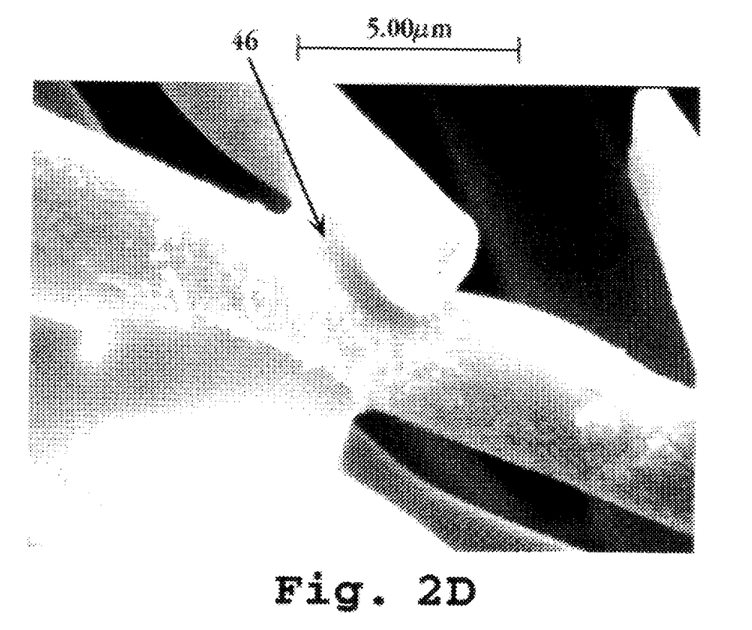

The junction region 46 at the lower center in FIG. 2C is shown at 7,000×magnification in FIG. 2D. The micrograph shows more clearly the textured grain-growth regions of the alumina fibers, and both silica/alumina and alumina/alumina fiber junctions.

Figure 3A:
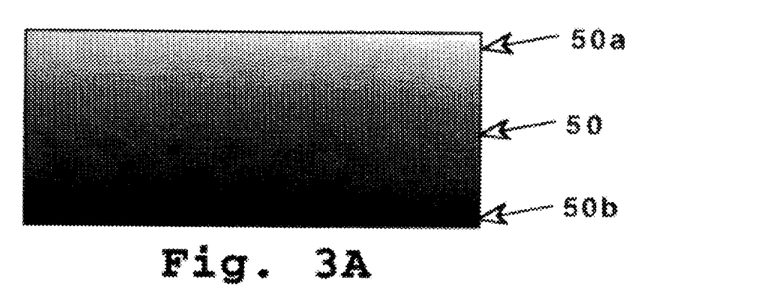
FIGS. 3A and 3B show a matrix having a continuous fiber-density gradient (FIG. 3A) and a discontinuous fiber-diameter gradient (FIG. 3B)

In the embodiments shown in Figs. 1A and 1B, the density of the matrix is uniform in each block or plate dimension. In a second general embodiment of the matrix, which is shown end-on at 50 in FIG. 3A, the matrix has a fiber density gradient progressing in the bottom-to-top direction. In a typical matrix, the gradient varies between a selected density in the range between 3.5–5.0 pounds/ft$^3$ in an "upper" matrix region 50a, to a selected density in the range between about 5.5 to 12 pounds/ft$^3$ in an opposite matrix region 50b.

Figure 3B:
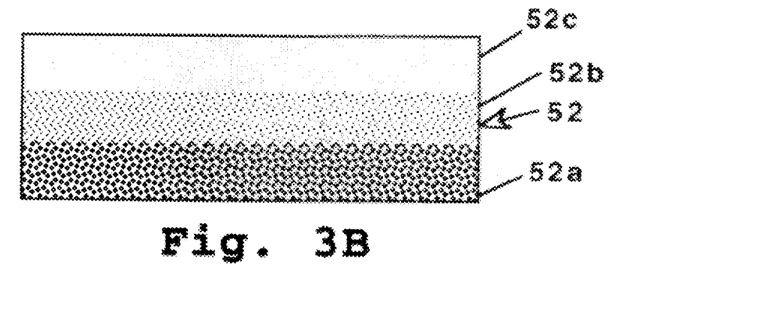

In another embodiment, the matrix has a discontinuous gradient of density, fiber sizes, and/or fiber composition. The embodiment illustrated end-on at 52 in FIG. 3B is formed of three stacked layers 52a–52c, each having a different fiber diameter. For example, the lower plate is formed of fused silica fibers having fiber diameters of a selected size in the size range between 1–3 µm; the middle layer, silica fibers of a selected size in the diameter size range between 3–5 µm; and the upper layer, silica fibers of a selected size in the size range between 5–20 µm.

In the matrix just described, larger-diameter fibers are associated with larger void or pore sizes in the matrix due to the different packing densities of the fiber at a given fiber-weight density. The dependence of pore or void size on fiber diameter is demonstrated by the mercury porosimetry study on matrices formed in accordance with the invention, with different fiber sizes.

Figure 4:
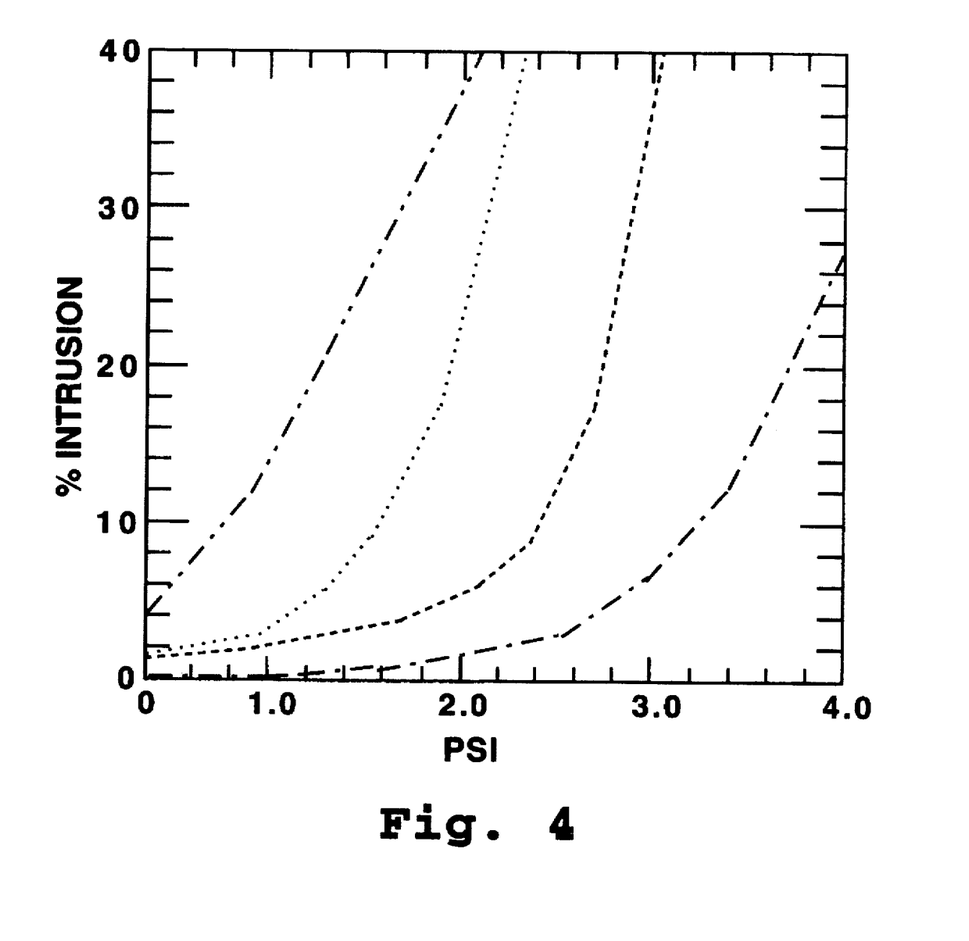
FIG. 4 is a plot showing percent mercury intrusion into matrices formed with fiber diameters of 1.3 µm (dash-dot line), 3 µm(dotted line), 6 µm (dash-2-dot line), and a mixture of 1.3 and 3 µm (dashed line), as a function of intrusion pressure.

In this study, the percent intrusion of mercury into a matrix, as a function of mercury intrusion pressure, was measured using a Micromeretics PoreSizer 9320 mercury porosimeter. Sample sizes with dimensions of 0.5625 inch diameter by 0.4 inch height were cored from a fused matrix block formed in accordance with the invention. The intrusion pressure was varied from 0.4 to 30 psi. FIG. 4 shows the observed intrusion vs psi curves, over the pressure range 0.4 to 4 psi, for matrices formed from silica fibers having diameters of 1.3 µm (dash-dot line), a mixture of 1.3 and 3 µm (dash line), 3 µm (dotted line), and 6 µm (dash-dot-dot line).

As seen, the percent intrusion is significantly higher, for a given intrusion pressure between 0.4 and 4 psi, for larger-diameter fibers, indicating that a matrix formed of such fibers has significantly larger pores or voids.

The discontinuous matrix shown in FIG. 3B may alternatively be formed of discontinuous plates having different fiber compositions, e.g., different silica/alumina weight ratios, or different fiber densities, or combinations of different fiber diameters, composition and density.

Figure 5A:
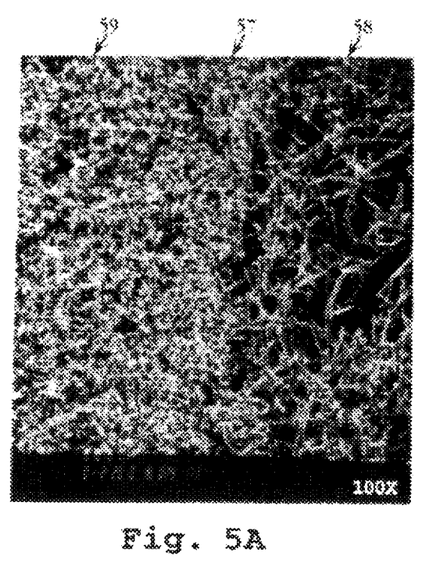
FIGS. 5A and 5B are computer generated images of scanning electron micrographs of a matrix constructed from different-density layers, taken at the interface region between plates of different density, at 100×(4A) and 500× (4B) magnification.
Figure 5B:
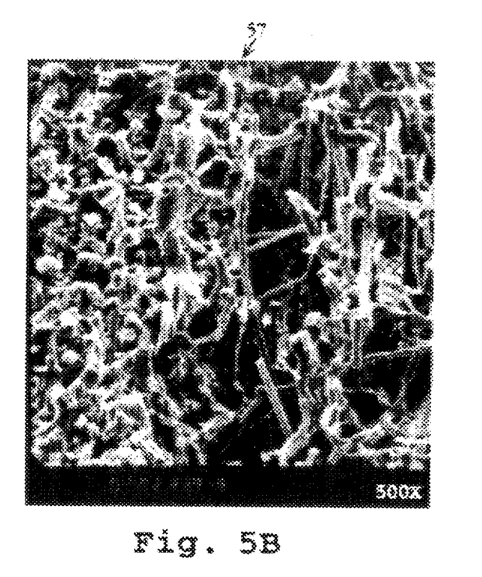

FIGS. 5A and 5B are computer generated images of scanning electron micrographs of a region of discontinuous, layered matrix 57 having different fiber-density layers, here showing a relatively low-density fiber layer 58 at the interface with a relatively high-density fiber layer 59, taken at 110×(FIG. 5A) and 500×(FIG. 5B) magnification. The figure shows the larger pore or void sizes in the lower-density layer, and also the fused-fiber connections at the layer interface.

II. Preparing the Matrix

This section describes the preparation of the matrix described in Section I, in accordance with another aspect of the invention. In general, the method includes forming a fiber slurry having desired viscosity and fiber dispersion characteristics, allowing the slurry to settle under conditions that produce a selected fiber density and orientation, drying the resulting fiber block, and sintering the block to form the desired fused-fiber matrix.

A. Fiber Treatment

The silica ($SiO_2$) and/or alumina ($Al_2O_3$) fibers used in preparing the matrix are available from a number of commercial sources, in selected diameters (fiber thicknesses) between about 0.5 µm–20 µm. A preferred silica fiber is a high purity, amorphous silica fiber (99.7% pure), such as fabricated by Manville Corporation (Denver, Colo.) and sold under the fiber designation of "Q-fiber". High purity alumina fibers (average 3 microns) may be procured, for example, from ICI Americas, Inc. (Wilmington, Del.).

In a preferred heat treatment, the silica fibers are compressed into panels, e.g., using a Torit Exhaust System and compaction unit. The compressed panels are passed through a furnace, e.g., a Harper Fuzzbelt furnace or equivalent, at 2200° F. for 120 minutes, corresponding to a speed setting of about 2.7 inches/minute. The heat treatment is used to close up surface imperfections on the fiber surfaces, making the matrix more stable to thermal changes on sintering. The heat treatment also improves fiber chopping properties, reducing fabrication time.

In a preferred method, the heat-treated fibers are washed to remove debris and loose particles formed during fiber manufacturing.

B. Preparing a Fiber Slurry

Silica and/or alumina fibers from above are blended to form a fiber slurry that is used in forming a "green-state" block that can be sintered to form the desired matrix.

The slurry is formed to contain, in an aqueous medium, silica, alumina, or silica and alumina fibers of the type described above, at a fiber:liquid weight ratio of between about 1:25 to 1:70, where the liquid weight refers to the liquid weight of the final slurry preparation.

The slurry preferably includes a thickening agent effective to give the slurry a viscosity between about 1,000 and 25,000 centipoise, as measured by standard methods (ref). The viscosity agent may be any of a number of wellknown hydrophilic polymers, such as polyvinylalcohol, polyvinylacetate, polyvinylpyrrolidone, polyurethane, polyacrylamide, food thickeners, such as gum arabic, acacia, and guar gum, and methacrylate type polymers. The polymers preferably have molecular weights greater than about 25–50 Kdaltons, and are effective to increase solution viscosity significantly at concentrations typically between about 0.5–10 weight percent solution.

Preferred thickening agents polymers that also have tacky or adhesive properties, such as methyl cellulose, terpolymers of maleic anhydride, alkyl vinyl ether, and an olefin (U.S. Pat. No. 5,034486), copolymers of ethylene and olefins (U.S. Pat. No. 4,840,739), cellulose-containing pastes (U.S. Pat. No. 4,764,548), and soy polysaccharides. One preferred thickening agent is methylcellulose, e.g., the polymer sold under the tradename Methocel A4M and available from Dow Chemical Co. (Midland, Mich.).

Where the matrix is formed of high-purity silica fibers and/or alumina, the slurry is also formed to contain a source of boron that functions, during sintering, to form a boron/silica or boron/alumina surface eutectic that acts to lower the melting temperature of the fibers, at their surfaces, to promote fiber/fiber fusion at the fiber intersections. In a preferred embodiment, the boron is supplied in the slurry as boron nitride particles 15 to 60 µm in size particles. Such particles can be obtained from Carborundum (Amherst, N.Y.). The amount of boron nitride is preferably present in the slurry in an amount constituting between about 2–12 weight percent of the total fiber weight.

The adhesive property of the thickening agent described above is useful in adhering particles of boron nitride and, if used, silicon carbide, to the fibers in the slurry, to produce a relatively uniform of particles in the slurry, and prevent the particles from settling out of slurry during the molding process described below.

Figure 6:
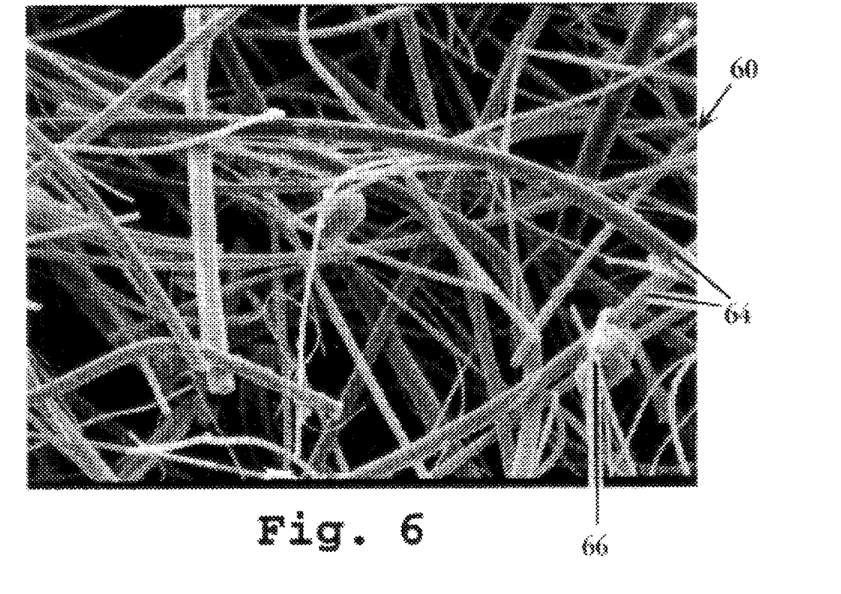
FIG. 6 is a computer generated image of a scanning electron micrograph which shows the distribution of boron nitride particles on representative silica fibers in the green-state block.

This is illustrated in FIG. 6, which shows a computer generated image of a scanning electron micrograph of a portion of a dried fiber block 60 of silica and/or alumina fibers 64 with boron nitride particles, such as particle 66, distributed over the fibers.

The even distribution of particles throughout the block is advantageous in achieving effective and relatively uniform boron concentrations throughout the matrix during sintering, as described below.

The slurry preferably also contains a dispersant which acts to coat the fibers and help disperse the fibers, both to increase slurry viscosity, and to prevent silica fibers from "bundling" and settling out of the slurry as fiber aggregates during the molding process described below. The dispersant is preferably one which imparts a significant charge and/or hydrophilicity to the fibers, to keep the fibers separated during slurry formation and settling during the molding process.

For use with silica fibers, ammonium salts are particularly useful as dispersants, because the ammonium cation is released from the matrix in the form of ammonia during matrix drying and/or sintering. Preferred ammonium salts are the salts of polyanionic polymers, such as ammonium polymethylmethacrylate, or the ammonium salt of other carboxylated polymers. One preferred dispersant agent is the ammonium polymethylmethacrylate polymer sold by R. T.

Vanderbilt under the tradename Darvan 821A. The polymer dispersant is preferably added to the slurry to make up between about 0.2 to 5 percent of the total liquid volume of the slurry.

The slurry may further contain between about 1–5 percent by weight silicon carbide particles, such as obtainable from Washington Mills Electro Minerals Corp. (Niagara Fall, N.Y.).

A preferred method for preparing a slurry of the type just described is detailed in Example 1. Briefly, heat-treated silica fibers are suspended in water at a preferred fiber:water ratio of about 1:300 to 1:800. The fiber slurry is pumped through a centrifugal cyclone to remove shot glass and other contaminants, such as high soda particles. The fiber cake formed by centrifugation is cut into segments, dried at 550° F. for at least 8 hours, and then broken into smaller chunks for forming the matrix.

Fragments of the silica fiber cake are mixed in a desired weight ratio with alumina fibers, and the fibers are dispersed in an aqueous solution containing the dispersing agent. At this point, the fibers are preferably chopped to a desired average fiber length in a low-shear/high-shear mixer. In general, the greater the degree of chopping, the shorter the fibers, producing better packing and a less open matrix structure. Similarly, longer fibers lead to more open matrix structure. The fiber mixing is preferably carried out under condition to produce average fiber sizes of a selected size in the 1–10 mm fiber-length range.

After mixing, the fibers are allowed to settle, and the liquid/fiber ratio is reduced by decanting off some of the dispersing liquid. To this slurry is added an aqueous gel mixture formed of the viscosity agent, e.g., methyl cellulose, and the matrix particles, e.g., boron nitride particles, and the slurry components are mixed to form the desired high-viscosity slurry. The slurry is now ready to be transferred to a casting mold, to prepare the green-state block, as described in the next section.

C. Forming a Dried Fiber Block

Figure 7A:
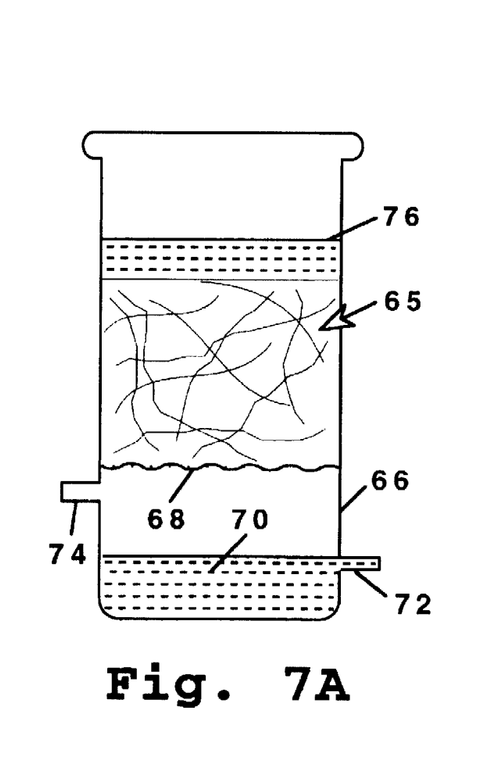
FIGS. 7A–7C illustrate steps in compacting a silica fiber slurry, in preparing a green-state fiber block, in the method of the invention.
Figure 7B:
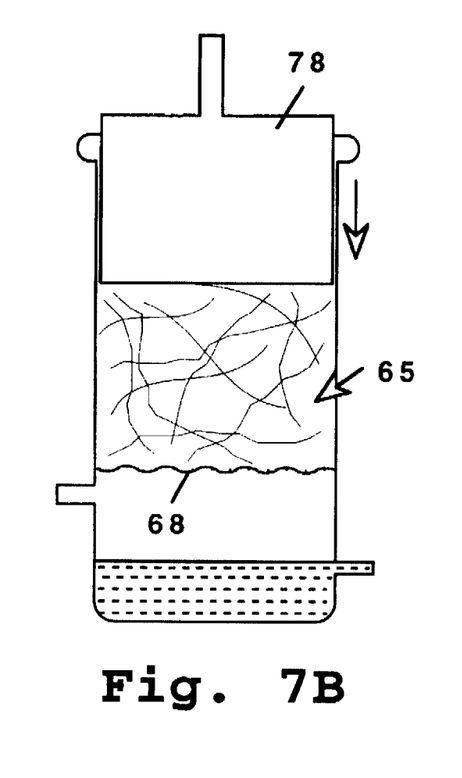
Figure 7C:
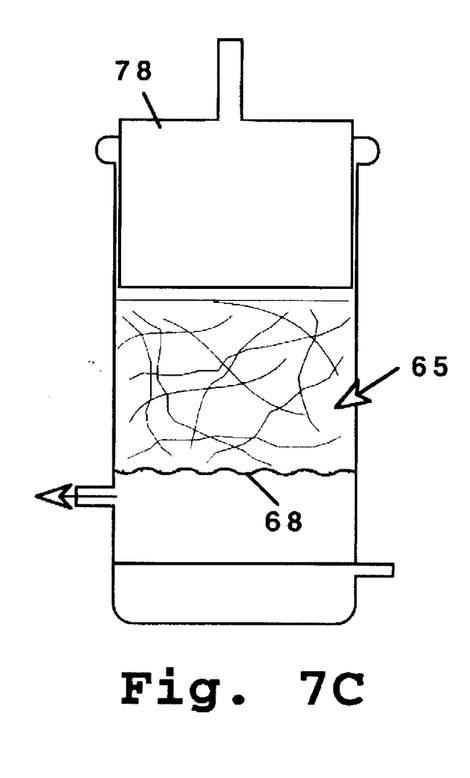

The method of forming a green-state block, i.e., a dried, rigid matrix of unfused fibers, from the above fiber slurry, is illustrated in FIGS. 7A–7C. According to an important aspect of the method, the slurry is allowed to settle and is dewatered in a fashion designed to achieve a relatively uniform fiber density throughout the matrix, and relatively randomly oriented fibers, i.e., with little fiber orientation preference in the direction of settling.

In the first step, illustrated in FIG. 7A, a slurry 65 is added to a mold 66 equipped with a lower screen 68 sized to retain slurry fibers. For fiber sizes in the range 1–10 mm, the screen has a mesh size between about 8 to 20 squares/inch. The mold has a lower collection trough 70 equipped with a drain 72 and a vacuum port 74 connected to a suitable vacuum source.

Initially, the slurry is added to the mold and, after stirring the slurry to release gas bubbles, is allowed to settled under gravity, until the level of water in the mold, indicated at 76 is about 1–2 inches above the level of the desired final compaction height, i.e., the final height of the dewatered block. For a slurry of about 12 l added to a 18 cm² square mold, the initial settling takes about 3–10 minutes.

The partially drained slurry in the mold is now compacted with a compacting ram 78 to force additional water slurry. This is done by allowing the ram to act against the upper surface of the slurry under the force of gravity, while draining the water forced through screen 68 from the mold. Water is squeezed from the slurry until the ram reaches the desired compaction height, as shown in FIG. 7B. With the slurry volume and mold dimensions just given, a ram having a weight of about 7 lbs is effective to compress the partially dewatered slurry in a period of about 0.2 to 2 minutes.

In the final step of compacting and dewatering, the drain is closed and vacuum is applied to port 74 until the block is completely dewatered. A vacuum of between about 0.01 to 0.5 atm is effective to produce complete dewatering of the mold in a period of about 0.2 to 5 minutes. As seen in FIG. 3C, the vacuum dewatering may result in the upper surface of the block pulling away from the ram.

The dewatered block is now removed from the mold and dried in an oven, typically at a temperature between 250°–500° F. In the dried matrix, the viscosity agent, and to a lesser extent, the dispersant agent, act to bond the fibers at their intersections, forming a rigid, non-fused block. The target density of the matrix after drying is between about 3.3 to 5.3 pounds/ft³. Details of the molding and drying steps, as applied to producing one exemplary silica/alumina fiber matrix, are given in Example 2, Parts A and B.

The green-state matrix may be formed to include sacrificial filler element(s) that will be vaporized during sintering, leaving desired voids in the final fused matrix block. The filler elements are preferably formed of polymer or graphite. As one example, 1A, an array of parallel rods (not shown) may be placed in the mold, at the time the slurry is added. Slurry settling and dewatering are as described above, to form the desired green-state block with the included sacrificial element.

Figure 8:
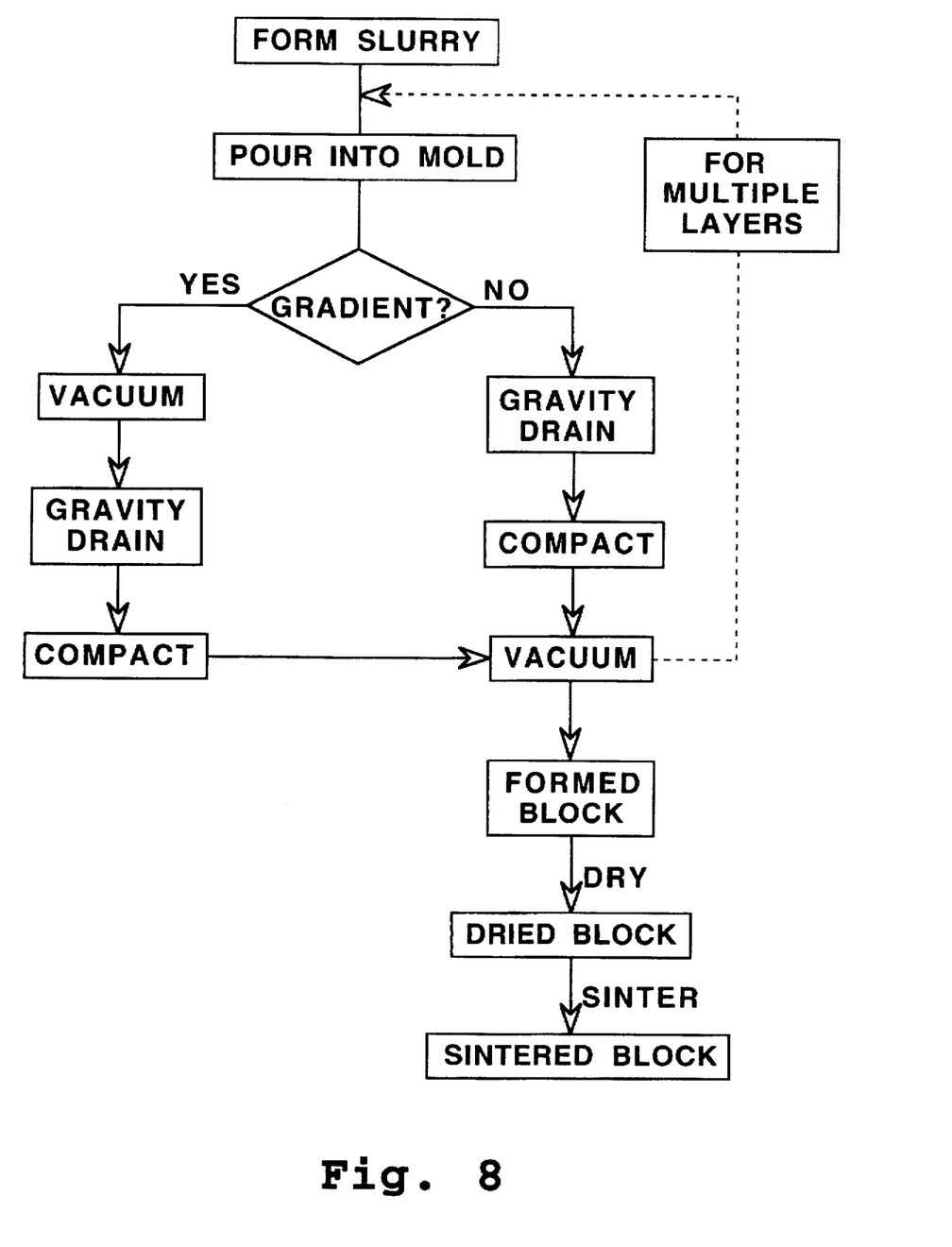
FIG. 8 is a flow diagram showing steps is forming a compressed slurry according to various embodiments of the method of the invention.

FIG. 8 is a flow diagram of settling and dewatering methods that are suitable for forming a uniform green-state matrix, according to the steps just described, or alternatively, for forming a gradient matrix such as described above with respect to FIGS. 3A and 3B.

The first step shown is the slurry formation. The slurry may be a single fiber suspension containing a desired size range and fiber composition. Alternatively, for forming a discontinuous or step fiber matrix, two or more slurries having different fiber thicknesses, densities, and/or fiber compositions may be formed.

With continued reference to the figure, after the slurry is introduced into the mold, the steps in settling and dewatering the slurry can be varied to produce either a continuous gradient of fiber density, as indicated at the left in the figure, or a uniform fiber density, as indicated at the right. The steps in forming a uniform gradient, including an initial settling step, followed by ram compaction and final dewatering by vacuum have been considered above.

To produce a continuous gradient of fiber densities, the slurry is first subjected by dewatering by vacuum, causing material closest to the screen to be compacted preferentially. When a desired gradient is achieved, the slurry is gravity drained to dewater the slurry, then ram-compacted for further dewatering. The slurry may be subjected to a final vacuum dewatering, as indicated.

To produce a block having a series of discontinuous layers, each with a uniform fiber density, each successive slurry is handled substantially as described above for the uniform-density block (at the right in FIG. 8). The layers can be formed by successively casting layer upon layer in the mold, with each successive layer being compacted as described above. Alternatively, a series of block layers, each with a distinctive fiber size/composition and/or density is prepared. Before drying, the individual blocks are placed together in layers, to form the desired discontinuous-layer block. The layers may be "glued" together before drying by applying, for example, a layer of boron nitride in the viscosity agent between the layers.

D. Fused Fiber Matrix

In the final step of matrix formation, the green-state block from above is sintered under conditions effective to produce surface melting and fiber/fiber fusion at the fiber crossings. The sintering is carried out typically by placing the green-state block on a prewarmed kiln car. The matrix is then heated to progressively higher temperatures, typically reaching at least 2,000° F, and preferably between about 2,200-2,400° F., until a desired fusion and density are achieved, the target density being between 3.5 and 5.5 pounds/ft$^3$. For a block formed solely of alumina fibers, a maximum temperature of about 2,350° F. is suitable. One exemplary heating schedule for a silica/alumina matrix is given in Example 2.

In a preferred method, discussed above, the matrix is formed with high-purity silica fibers that contain little or no contaminating boron and/or with alumina fibers that are also substantially free of boron. In order to achieve fiber softening and fusion above 2,000° F., typically in the temperature range 2,000-2,200° F., it is necessary to introduce boron into the matrix during the sintering process, to form a silica/boron or alumina/boron eutectic mixture at the fiber surface. Boron is preferably introduced, as detailed above, by including boron nitride particles in the green-state block, where the particles are evenly distributed through the block.

During sintering, the boron particles are converted to gaseous $N_2$ and boron, with the released boron diffusing into the surface of the heated fibers to produce the desired surface eutectic, and fiber fusion. The distribution of boron particles within the heated block ensures a relatively uniform concentration of boron throughout the matrix, and thus uniform fusion properties throughout.

Also during fusion, the viscosity agent and dispersant agents used in preparing the green-state block are combusted and driven from the block, leaving only the fiber components, and, if added, silicon carbide particles.

Where the green-state block has been constructed to include a sacrificial element, the sintering is also effective to vaporize this element, leaving desired voids in the matrix, such as a lattice of channels throughout the block.

After formation of the fused-fiber matrix, the matrix block may be machined to produce the desired shape and configuration. For example, the matrix of FIG. 1A can be formed by drilling an array of channels in the block; the matrix of FIG. 1B can be formed by cutting the block into thin plates.

III. Polymer Fiber Matrix

Figure 9A:
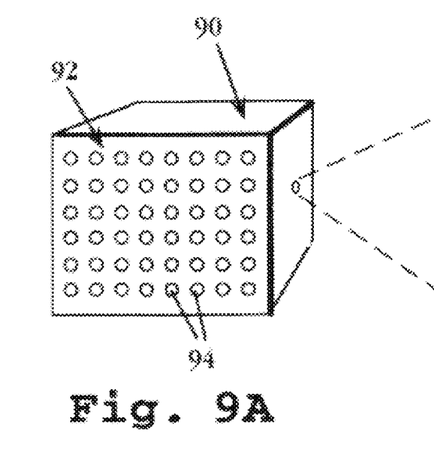
FIGS. 9A and 9B show a polymer-fiber matrix constructed in accordance with another embodiment of the invention.
Figure 9B:
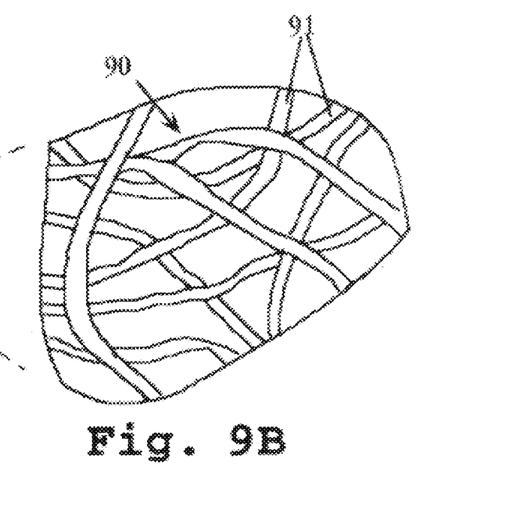

In another aspect, the invention includes a fibrous polymer matrix, such as the matrix 90 shown in FIG. 9A. The matrix is composed of fused polymer fibers, and is characterized, in dry form, by: (a) a rigid, three-dimensionally continuous network of open, intercommunicating voids, and (b) a free volume of between about 90–98 volume percent. That is, the matrix has substantially the same microscopic structure illustrated in FIG. 2A–2D, but where the fibers include polymer fibers, indicated at 91 in FIG. 9B. The fibers may also include up to 80 percent by weight of either silica fibers, alumina fibers, or a combination of the two fibers types.

The matrix shown in FIG. 9A is designed for use particularly as a substrate for cell growth in vitro, and as such, contains an array 92 of channels, such as channels 94, extending through the matrix, as described with respect to FIG. 1A. In an alternative embodiment, the matrix has the multi-plate configuration shown for a silica matrix in FIG. 2B.

The fused polymer matrix is formed substantially as described for the silica, alumina, or silica/alumina fiber matrices described above, but with the modifications now to be discussed.

The polymer fibers used in constructing the matrix may be any thermoplastic polymers that can be heat fused, typically when heated in the range 400–800° F. Exemplary polymer fibers include polyimide, polyurethane, polyethylene, polypropylene, polyether urethane, polyacrylate, polysulfone, polypropylene, polyetheretherketone, polyethyleneterphthalate, polystyrene, and polymer coated carbon fibers. Fibers formed of these polymers, and preferably having thickness in the 0.5 to 20 µm range, can be obtained from commercial sources. The fibers may be chopped, i.e., by shearing, to desired lengths, e.g., in the 0.1 to 2 mm range, by subjecting a suspension of the fibers to shear in a high-shear blender, as described above.

The polymer fibers may be blended with up to 80 weight percent silica and/or alumina fibers of the type described above. Preferably, the silica fibers are heat treated to close up surface imperfections on the fiber surfaces, as described above. The alumina fibers may also be heat treated, e.g., under the sintering conditions described above, to produce the surface granulation on the fiber seen in FIGS. 2C and 2D.

The aqueous fiber slurry used in preparing the matrix contains, in addition to fibers, a viscosity agent effective to produce a final slurry viscosity between about 1,000 and 25,000 centipoise. Viscosity agents of the type mentioned above are suitable. If the polymers fibers are relatively hydrophobic, or if the fibers include silica fibers, the slurry should contain a dispersant effective to prevent the fibers from aggregating on settling. Such a dispersant may include surfactants and/or charged polymers, and/or block copolymers, such as polyethylene/polypropylene block copolymers known to enhance the hydrophilicity of polymer surfaces.

The slurry also contains an adhesive agent effect to retain the green-state fiber network in a rigid condition once it is formed. Either the viscosity agent or dispersant may supply the necessary adhesive properties. Alternatively, a separate adhesive component may be added to the slurry.

The above slurry is placed in a settling mold, as above, and the fibers are allowed to settle under dewatering conditions, substantially as described above, to yield randomly oriented fibers having a desired fiber density. The network is formed into a greenstate block by drying, e.g., at 100–300° F.

In the final step, the greenstate block is heated under conditions, typically at a temperature between 400°–800° F., effective to produce fiber fusion at the fiber points of intersection. The selected temperature is near the softening point of the thermoplastic polymer. At this temperature, the polymer fibers fuse with one another and with silica and/or alumina fibers in the block to produce the desired rigid, fused fiber matrix.

IV. Utility: Cell-Growth Substrate

The low-density matrix described above in Sections I–III is designed particularly for use as a substrate for cell growth in vitro, or in vivo as an implantable substrate.

The architecture of the matrix, and particularly the characteristics of a rigid, three-dimensionally continuous network of open, intercommunicating voids, and a free volume of between about 90–98 volume percent, permit rapid cell growth in three dimensions.

In a preferred embodiment, the matrix is formed of silica fibers, typically in an amount between about 50–100 weight percent of the total fiber weight. In another preferred embodiment, the matrix is formed to include alumina fibers, preferably heated to produce surface granulation, in an amount of fiber preferably between about 20–80 weight percent fiber.

The silica and/or alumina fibers may enhance cell adhesion, and/or adhesion of growth factors, such as fibrofectin, vibronectin, or fibrinogen. Representative cell culture and cell implantation applications are discussed below.

A. Cell Culture

Figure 10A:
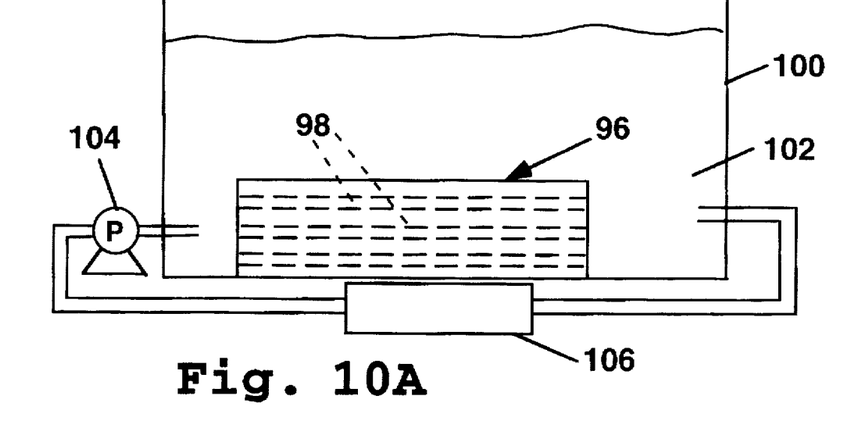
FIGS. 10A–10C illustrate three cell culture systems employing various matrix embodiments of the invention.
Figure 10B:
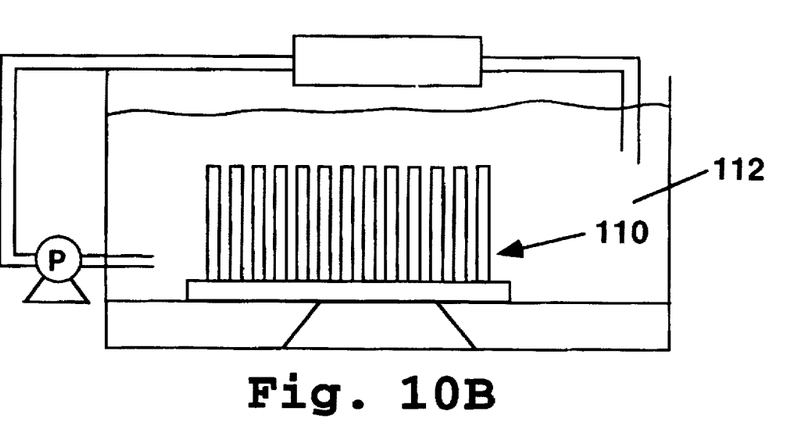
Figure 10C:
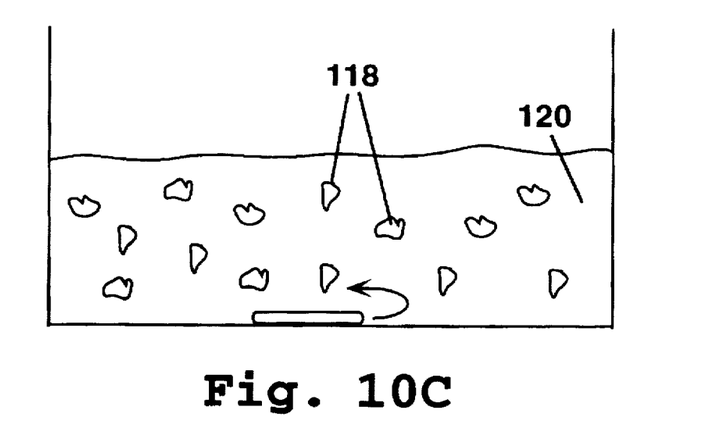

In one general embodiment, the matrix of the invention is used to support cell growth in a cell culture system in vitro. FIGS. 10A–10C illustrate three cell culture configurations, in accordance with the invention. The configuration illustrated in FIG. 10A uses a fiber matrix 96 of the type shown in FIG. 1A, having a lattice of channels, such as channels 98, extending through the matrix. The matrix is supported in a culture vessel 100 partially filled with culture medium 102. The medium is pumped into and through the matrix, as indicated, by a pump 104. The system further includes a filter 106 placed in-line with the pump for extracting desired cell products and/or purifying the medium of cell bi-products. Suitable heating and gas-supply means for maintaining desired gas and temperature control of the medium may also be employed, as well as means for replenishing the medium. FIG. 10B shows a cell culture configuration which utilizes the a multi-plate matrix, like the one shown in FIG. 1B, and indicated here at 110. As shown, the plates in the matrix are submerged in a suitable cell culture medium 112 in a vessel 114, and the medium is circulated, through the plates by a pump 116. The configuration may also include a filter and culture control means, as indicated above.

In a third configuration, shown in FIG. 10C, the matrix is present as fragments, such as fragments 118, which are suspended in a culture medium 120. The matrix fragments are produced preferably by fragmentizing matrix plates of having a thickness between about 0.2 to 2 mm. The matrix fragments, being slightly denser than the culture medium, can be maintained in a suspended state, by gentle stirring or gas bubbling, and can be separated readily from the medium by settling, centrifugation or filtration.

It will be understood that the matrix in the configurations is first sterilized, conventionally, and may be further treated to preabsorb agents which promote cell adhesion to the substrate. Typically these agents include a divalent cation, such as $Mg^{+2}$, and a glycoprotein such as fibronectin, polyethylene, and/or fibrinogen. The pretreatment preferably involves incubating the sterilized matrix in a serum or other medium containing the growth factors of interest.

Alternatively, the fibers, meaning either silica or polymer fibers, may be derivatized by covalent attachment of desired growth factors, such as bone osteogenic factor, cytokines, or the like. Methods for derivatizing the free hydroxyl groups on silica fibers, or free hydroxyl, amine, carboxyl, sulfhydryl, or aldehyde groups that may be present on polymer fibers are well known.

B. Implantable Cell Matrix

Figures 11, 12:
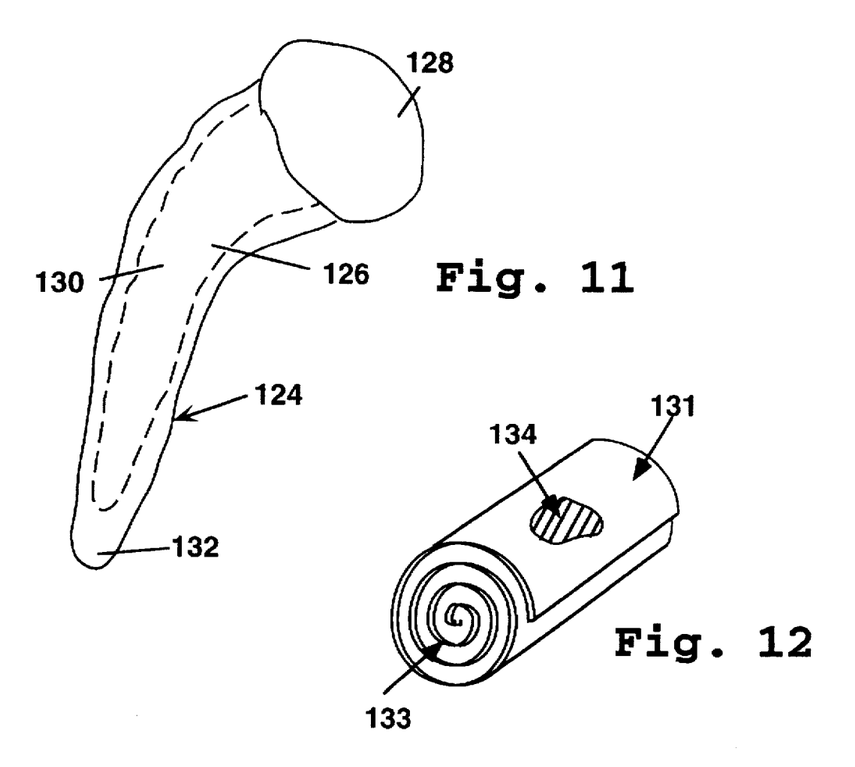
FIG. 11 shows a prosthetic device containing a matrix cap constructed in accordance with the invention.
FIG. 12 shows an implantable cell matrix device constructed in accordance with the invention.

In another general application, the matrix of the invention is used as an implantable substrate for supporting cell growth in vivo. FIG. 11 shows, as one example of this application, a hip replacement device 124 having a stem 126 designed to be inserted and locked into the femur of subject, and a ball 128 which will serve as the ball of the repaired hip joint. The stem has a titanium inner core 130 which is formed integrally with the ball. The cover is ensheathed in a fused-fiber matrix 132 constructed according to the invention, and which forms a covering over the core. The matrix covering is preferably formed by machining a fused-fiber block of the type described above. The covering may be attached to the stem core by a suitable adhesive, or by heat fusion near the melt temperature of the titanium, in the case of a silica and/or alumina fiber matrix.

In operation, the matrix on the stem provides a substrate for the growth and infusion of osteoblast cells, acting to weld the stem to the bone through a biological bone structure. The matrix fibers may include bone growth factors for promoting bone cell growth into the matrix.

FIG. 12 shows an implantable cell substrate device 131 also constructed according to the invention. The device is designed for use as an implantable substrate for supporting growth of a selected tissue cells, such as pancreatic cells or fibroblasts, capable of producing desired cell metabolites such as insulin or interferon.

The device illustrated has a tubular construction, and provides a spiraled inner core 133 for supporting cell growth, while allowing body fluids to bathe the cells, bringing nutrients and removing cell products. The device is formed preferably by machining a block of fused-fiber matrix of the type disclosed herein. The outer surface of the device is coated with a biocompatible material, such as silicon rubber, as indicated at 134 to insulate the fiber matrix from direct contact with the surrounding tissue.

In operation, the device is seeded with the desired cells in culture, preferably until the spiraled core has a maximum cell density. The device is then implanted into a desired tissue region, e.g., an intramuscular site.

The two examples described above illustrate two of a variety of implant devices, for bone repair, bone replacement, and tissue-cell augmentation or replacement that may be prepared using the cell-substrate matrix material of the invention.

V. Utility: Chromatography

The silica-fiber matrix of the invention is also useful for chemical and cell chromatographic separations.

In one embodiment, the matrix can serve as a substrate for thin-layer chromatographic separations, using well-known solvent-systems and development conditions. The matrix in this application is preferably a thin matrix plate, formed, for example, by slicing a matrix block to a desired thickness, e.g., between 1–3 mm. Alternatively, thin plates may be prepared by slurry settling, as described above, in thin-plate molds.

In a related aspect, the matrix serves the role of a silica gel column for chemical separations by silica gel chromatography. As above, the matrix may be machined from a block matrix mold, or formed by settling in a suitable cylindrical mold. For both applications, the density of the matrix is preferably above the 3.5–5.5 pounds/ft$^3$ matrix density that is employed for cell culture.

According to another aspect of the invention, the fused-fiber matrix material having a density between about 3.5 and 5.5 pounds/ft$^3$ is useful for cell-separation chromatography, and typically for use in separating cells and other particles above about 1 micron in size from serum components in a blood sample.

Figure 13A:
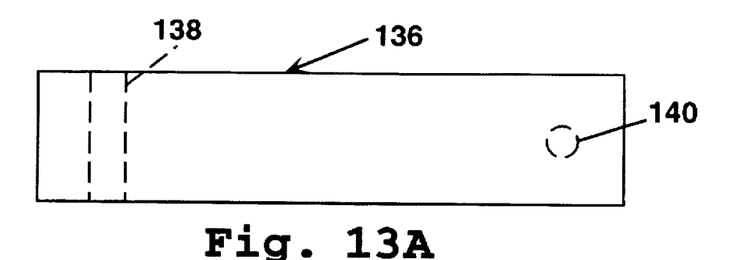
FIG. 13A and 13B illustrate the use of the invention for blood-sample separation in a diagnostic device.
Figure 13B:
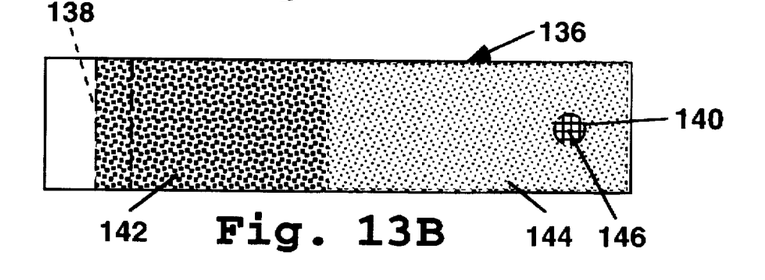

As an example, FIGS. 13A and 13B illustrate a diagnostic test strip 136 for use in detecting a serum components, such as glucose, cholesterol, or a cholesterol-containing lipoprotein, such as low density lipoprotein or high-density lipoprotein particles. The strip, which is formed of the fused-silica fiber matrix material of the invention, includes an application site 138 at one strip end a detection site 140 at the opposite end. The detection site may include reagents for producing a detectable color signal in the presence of a selected serum analyte. Alternatively, serum from this site may be transferred by physical contact to a separate reagent pad.

In operation, a blood sample, e.g., a 25–200 μl sample, is added to the application site, and the sample is drawn by capillarity toward the strip's opposite end. Migration of the sample through the interstices of the matrix acts to retard the migration rate of larger particles, including blood cells, causing separation of the blood cells separated into a slower migrating blood cell fraction 142 and a faster-migrating serum fraction 144, which is received at the detection site free of blood cells. Analyte detection may occur at this site, as indicated at 146, or a separate detection pad may be brought in contact with the strip site, to draw serum into the pad.

The following examples illustrate methods of preparing silica, alumina and silica/alumina fused-fiber matrices in accordance with the invention. The examples are intended to illustrate, but in no way limit, the scope of the invention.

EXAMPLE 1

Forming a Fiber Slurry

A. Fiber Pretreatment

Silica fibers were heat treated as described above. The heat-treated silica fibers and/or alumina fibers were dispersed in deionized water at a fiber to deionized water ratio of 1:300 to 800 by weight. The actual deionized water amount was converted into a volume for ease of measuring. Approximately 150 pounds of fibers was mixed with 900 gallons of slurry and was pumped through a centrifugal hydrocyclone (Bauer Brothers Centrifugal Cleaner) to remove glass shots and other high density, high sodium contaminates. The "clean" fiber was collected in a centrifuge, where it was formed into a "cake" and dewatered. The fiber cake was then cut into segments. The segments were oven dried at 550° F. for a minimum of 8 hours. Dried segments were broken into smaller chunks and weighed out to the desired amounts for matrix processing.

B. Preparation of Gel Stock A gel stock was prepared for dispersing the boron nitride and/or silicon carbide powders into the fiber slurry. A 2 parts by weight methyl cellulose (Methocel A4M commercial grade powder from Dow Chemical Co.) was dissolved in 98 parts by weight, of hot deionized water (1 megohm) and vigorously stirred to produce a homogeneous solution. The methyl cellulose solution was slowly gelled by placing the mixture container in an ice bath with a maximum temperature of 45° F., for a minimum time of 40 minutes. Upon completion of gelling, the solution's viscosity was measured using a Brookfield Synchro-Lectric Viscometer (Model LVT) with a number 1 spindle installed in the instrument. Prior to testing the appropriate sample size was adjusted for temperature to 68°+2° F. while stirring slowly to avoid air entrapment. Viscosity measurements were recorded at one spindle speed (0.6 rpm) and expressed in centipoise. The solution should have a minimum viscosity of about 4000 centipoise.

C. Preparing a Fiber Suspension

A suspension paste of boron nitride, silicon carbide, and gel stock from Part B above was prepared by thoroughly mixing the constituents together. The weight percentages of the boron nitride was measured from between 2 and 12 percent of the total fiber weight. The silicon carbide concentration was measured from 1 to 5 percent by weight of the total fiber weight of the matrix. The methyl cellulose (methocel A4M) concentration was determined by the weight of boron nitride to be dispersed. The methyl cellulose to boron nitride ratio can vary from between 0.2 to 1.5. The methyl cellulose concentration was measured in weight of gel stock as shown below:

| | |
|---|---|
| Gel Stock | 60–80% |
| Boron Nitride[a] | 12–35% |
| Silicon Carbide[b] | 5–8% |

[a] 325 Grit, SHP; Carborundum
[b] 600 Grit, SIKI I; Washington Mills

D. Mixing the Fibers

The silica, alumina, and/or polymer fibers were placed into the mixing container of a variable speed low-shear/high-shear mixer (preferably a double planetary type mixer). The dispersing agent was prepared by mixing 0.2 to 5% by volume solution of Darvan 821A (ammonium polymethylmethacrylate; R. T. Vanderbilt) and deionized water. A dispersing liquid was poured on top of the fibers in a ratio from 25:1 to 70:1 parts by weight liquid to fiber. The fibers were mixed into a slurry, and the slurry allowed to settle for an appropriate amount of time. Then the liquid to fiber ratio was reduced by decanting off some of the dispersing liquid.

The boron nitride, silicon carbide, gel stock suspension was added and blended into the slurry, and the slurry transferred to a casting mold.

EXAMPLE 2

Preparation of Fused-Fiber Matrix

A. Casting the Fiber Slurry

The casting mold used to form the matrix is equipped with a hydraulic bottom, top or combination ram, gravity drain, and vacuum drain capability. Before the fiber slurry was transferred into the casting tower, the tower was rinsed with deionized water. All drain valves were then closed and deionized water was added to the mold to bring the water level one to two inches above the top of the bottom ram plate. The ram was actuated to remove any air bubbles from below the ram. The gravity drain valve was then opened to bring the water level to one-half inch above the top of the bottom ram plate.

The slurry was transferred to the mold, and stirred slowly with a plastic paddle in circular motions to remove any air bubbles. The top lid was secured and the slurry was gravity drained to remove most of its liquid. The matrix was then compressed to the desired compression height, and vacuum was applied to completely dewater the compressed structure. The matrix was removed from the mold.

B. Drying the As-Cast Matrix

The as-cast matrix was placed on an Armalon lined baker's type cart, and dried in an electrically heated drying oven at 350° F. for a minimum of 16 hours. The target density of the matrix after drying is between 3.3 to 5.3 pcf.

C. Fusion of the Matrix

The dried matrix was sintered about 2200° F. using a bottom loading Harper Elevator Kiln or equivalent; equipped with a programmable controller, to achieve fired densities between 3.5 to 5.5 pcf. Kiln cars were pre-warmed to increase temperature uniformity in the kiln and around the materials being fired. The firing schedule includes the following ramp rates, temperature settings, and estimated soak times.

| Ramp | Temperature | Soak Time |
|---|---|---|
| 2° F./minute | 1800° F. | 60 minutes |
| 2° F./minute | 1900° F. | 6 minutes |
| 1° F./minute | 2100° F. | 6 minutes |
| 2° F./minute | 2200° F. | as required to achieve target density |

The kiln was then cooled to 1800° F. prior to removal from the kiln car.

EXAMPLE 3

All Silica Fiber System 225 grams of high purity (99.68+%) heat treated silica fibers (Schuller, 108Q fibers, 1.2 µm to 1.5 µm in diameter) were dispersed in 12 liters of a 0.4% volumetric solution of Darvan 821A (R. T. Vanderbilt) and deionized water mixture and mixed for 2 minutes using a low shear double propeller mixer. 12.6 grams Boron Nitride Powder (325 mesh, Type SHP, Carborundum) was mixed into 60 grams of a 2% A4M Methocel (Dow Chemical) and deionized water solution.

The boron nitride/Methocel suspension was added to the silica slurry and mixed into the fiber slurry using a low shear double propeller mixer for another 2 minutes. The slurry was cast in a top open 7"×7" mold with a stiff screen bottom. The slurry was allowed to gravity drain at a rate of 0.9 inches/minute. A compression plunger was allowed into the mold when the settling slurry reached 2" above the desired block height. The plunger was stopped to a height of 4.5" from the bottom of the mold, as liquid was still draining from the billet. After nine liters of liquid had been removed from the cast block, vacuum assisted draining was used to remove one more liter.

The block, 7"×7"×4.5" in size, was removed from the mold and dried for a minimum of 12 hours at 125° C. The dry density of the block was 4.30 pfc (0.07 g/cc). The block was fired at a ramp rate of 2° C./minute to 1250° C. for 30 minutes. The fired density of the block was 5.32 pcf (0.08 g/cc).

EXAMPLE 4

78% Silica Fiber and 22% Alumina Fiber System 176 grams of high purity (99.68+%) heat treated silica fibers (Schuller, 108Q fibers, 1.2 µm to 1.5 µm in diameter) and 49 g of alumina fibers (2.5 to 3.5 microns in diameter, ICI America) were dispersed in 12 liters of a 0.4 % volumetric solution of Darvan 821A (R. T. Vanderbilt) and deionized water mixture and mixed for 2 minutes using a high shear Cowles dissolver mixer at 24,000 rpm. The slurry was allowed to age and settle for at least 4 hours. Approximately 2 liters of liquid was removed from the slurry.

12.6 grams of Boron Nitride Powder (325 mesh, Type SHP, Carborundum) and 4.3 grams Silicon Carbide Powder (Washington Mills, 600 Grit, SIKA 1) were mixed into 40 grams of 2% A4M Methocel (Dow Chemical) and deionized water solution. The boron nitride/Methocel suspension was added to the silica/alumina fiber slurry and mixed in using a low shear double propeller mixer for 2 minutes. The slurry was cast in a top open 7"×7" mold with a stiff screen bottom. The slurry was allowed to gravity drain at a rate of 0.7inches/minute. A compression plunger was lowered into the mold when the settling slurry reached 2 inches above the desired block height. The plunger was stopped to a height of 4.75 inches from the bottom of the mold, as liquid was still draining from the billet. After several liters of the liquid had been removed from the cast block, vacuum assisted draining was used to remove one more liter.

The block, 7"×7"×4.75" in size, was removed from the mold and dried for a minimum of 12 hours at 125° C. The dry density of the block was 4.30 pfc (0.07 g/cc). The block was fired at a ramp rate of 2° C./minute to 1250° C. for 45 minutes. The fired density of the block was 4.89 pcf (0.08 g/cc).

EXAMPLE 5

78% Silica Fiber and 22% Alumina Fiber System 176 grams of high purity (99.68%) heat treated silica fibers (Schuller, Code 112Q, 2.51 to 3.81 µm in diameter) and 49 grams of alumina fiber (2.5 to 3.5 microns in diameter, ICI America) were dispersed in 12 liters of 0.4% volumetric solution of Darvan 821A (R. T. Vanderbilt) and deionized water mixture and mixed for 1 minute using a high shear Cowles dissolver mixer at 24,000 rpm. The slurry was allowed to age and settle for at least 4 hours. Approximately 2 liters of liquid was removed from the slurry.

12.6 g Boron Nitride Powder (325 mesh, Type SHP, Carborundum) were mixed into 40 grams of a 2% ArM Methocel (Dow Chemical)/Deionized water solution. The boron nitride/Methocel suspension was added to the silica/alumina fiber slurry and mixed in using a low shear double propeller mixer for 2 minutes. The slurry was cast in a top open 7"×7" mold with a stiff screen bottom. The slurry was allowed to gravity drain at a rate of 0.7 inches/minute. A compression plunger was lowered into the mold when the settling slurry reached 3 inches above the desired block height. The plunger was stopped to a height of 5.0 inches from the bottom of the mold, as liquid was still draining from the billet. After several liters of liquid had been removed from the cast block, vacuum assisted draining was used to remove one more liter. The block, 7"×7"×5.0" in size, was removed from the mold and dried for a minimum of 12 hours at 125° C. The dry density of the block was 3.71 pcf (0.06 g/cc). The block was fired at a ramp rate of 2° C./minute to 1250° C. for 45 minutes. The fired density of the block was 3.85 pcf (0.06 g/cc).

EXAMPLE 6

All Alumina Fiber System 225 grams of alumina fiber (ICI America, 2.5 µm to 3.5 µm in diameter) were dispersed in 12 liters of a 0.06% volumetric solution of Darvan 821A (R. T. Vanderbilt) and deionized water mixture and mixed for 2 minutes using a high shear Cowles dissolver mixer. 23 grams Boron Nitride Powder (325 mesh, Type SHP, Carborundum) were mixed into 80 grams of a 2% A4M Methocel (Dow Chemical)/Deionized water solution. The boron nitride/Methocel suspension was added to the silica slurry and mixed in using a low shear double propeller mixer for 0.5 minutes. The slurry was allowed to gravity drain at a rate of 0.5 inches/minute. A compression plunger was lowered into the mold when the settling slurry reached 2 inches above the desired block height. The plunger was stopped to a height of 5.0 inches from the bottom of the mold, as liquid was still draining from the billet. After nine liters of liquid had been removed from the cast block, vacuum assisted draining was used to remove one more liter. The block, 7"×7"×5.0" in size, was removed from the mold and dried for a minimum of 12 hours at 125° C. The dry density of the block was 4.17 pcf (0.07 g/cc). The block was fired at a ramp rate of 2° C./minute to 1350° C. for 60 minutes. The fired density of the block was 4.32 pcf (0.07 g/cc).

While the invention has been described with reference to specific methods and embodiments, it will be appreciated that various modifications and changes may be made without departing from the invention.

It is claimed:

1. A method of producing a rigid fused-fiber matrix formed of fused fibers of silica, alumina, or silica and alumina, and having (a) a rigid, three-dimensionally continuous network of open, inter-communicating voids formed randomly in all directions, (b) a density of between about 3.5 and 5.5 pounds/cubic foot, and (c) a free volume of between about 90 –98 volume percent, said method comprising;

forming a slurry composed of (i) silica, alumina or silica and alumina fibers having selected fiber thicknesses in the size range between about 0.5 and 20 μm and fiber lengths between about 1 and 10 mm, at a fiber:liquid weight ratio of between about 1:25 to 1:70, (ii) a thickening agent effective to give the slurry a viscosity between about 1,000 and 25,000 centipoise, (iii) boron nitride particles, in an amount between about 2–12 percent by weight of the total fiber weight, and (iv) where the slurry contains silica fibers, a dispersing agent effective to enhance the dispersion of silica fibers in the slurry, allowing the slurry to settle in a mold under conditions effective to produce a fiber block having a selected fiber density between about 3.3 and 5.3 pounds/ft$^3$, drying the settled block to form a substantially dehydrated fiber block, and heating the dehydrated block to a temperature of at least about 2200° F. for a period sufficient to cause the fibers to form a fused-fiber matrix.

2. The method of claim 1, wherein said slurry is prepared with silica fibers having a thickness between about 1–20 μm.

3. The method of claim 1, wherein the slurry is prepared with alumina fibers having a fiber thickness between about 1–20 μm.

4. The method of claim 1, wherein the slurry is prepared to include both silica and alumina fibers, and the amount of alumina fibers is between 5–95 percent by weight of the total fiber weight.

5. The method of claim 1, wherein the thickening agent also enhances the binding of boron nitride particles to fibers in the slurry.

6. The method of claim 5, wherein thickening agent is methyl cellulose, at a methyl cellulose/boron nitride weight ratio of between 0.05 and 1.5.

7. The method of claim 1, further comprising placing filler elements, formed of graphite or polymer, in the mold, prior to the settling of said slurry, to form in the fiber block a lattice of linked strands of graphite or polymer, and in said heating to at least about 2200° F. , vaporizing said strands to leave a lattice of interconnected channels through which liquid medium can be circulated through the interior of the matrix.

8. The method of claim 1, further comprising placing filler elements, formed of graphite or polymer, in the mold, prior to the settling of said slurry, to form in the fiber block a series of graphite or polymer spacers, and in siad heating to at least about 2200° F. vaporizing said spacers to leave a series of matrix plates separated by voids through which liquid medium can be brought into contact with the sides of the plates.

9. The method of claim 1, wherein said slurry is allowed to settle in the mold under conditions effective to produce a fiber-density gradient in the direction of settling.

10. The method of claim 1, wherein, to form said slurry, two or more slurries composed of (i), (ii), (iii) and (iv) having different fiber thicknesses, densities, or compositions are prepared and allowed to settle successively in the mold, to form a matrix having a discontinuous gradient of density or layers of different compositions.

11. The method of claim 1, which further includes derivatizing the silica fibers of the fused-fiber matrix and attaching anti-ligand molecules to the derivatized fibers.

* * * * *